(12) United States Patent
Pahl (10) Patent No.: US 12,249,084 B2
(45) Date of Patent: Mar. 11, 2025

(54) SYSTEMS AND METHODS FOR MEDICAL IMAGERY ENHANCEMENT BY USE OF IMAGE GUIDANCE SYSTEM

(71) Applicant: Medtronic Navigation, Inc., Louisville, CO (US)

(72) Inventor: Robert Pahl, Broomfield, CO (US)

(73) Assignee: Medtronic Navigation, Inc., Lafayette, CO (US)

( * ) Notice: Subject to any disclaimer, the term of this patent is extended or adjusted under 35 U.S.C. 154(b) by 411 days.

(21) Appl. No.: 17/649,838

(22) Filed: Feb. 3, 2022

(65) Prior Publication Data

US 2022/0262018 A1 Aug. 18, 2022

Related U.S. Application Data

(60) Provisional application No. 63/149,739, filed on Feb. 16, 2021.

(51) Int. Cl.
*G06T 7/30* (2017.01)
*G06T 7/20* (2017.01)
*G06T 7/70* (2017.01)

(52) U.S. Cl.
CPC ............ *G06T 7/30* (2017.01); *G06T 7/20* (2013.01); *G06T 7/70* (2017.01); *G06T 2200/04* (2013.01); *G06T 2207/30004* (2013.01)

(58) Field of Classification Search
CPC .... G06T 7/30; G06T 7/20; G06T 7/70; G06T 2200/04; G06T 2207/30004; G06T 2207/10081; G06T 2207/10088; G06T 2207/30196; G06T 7/33; G06T 7/246; A61B 6/486; A61B 6/5264; A61B 6/547
See application file for complete search history.

(56) References Cited

U.S. PATENT DOCUMENTS

| | | | |
|---|---|---|---|
| 10,702,188 B2 | 7/2020 | Addison et al. | |
| 2009/0046906 A1 * | 2/2009 | Wohlgemuth | A61B 6/4476 382/128 |
| 2011/0123083 A1 | 5/2011 | Ojha et al. | |

(Continued)

FOREIGN PATENT DOCUMENTS

| CA | 3050809 A1 * | 9/2018 | ........... G06T 7/0016 |
|---|---|---|---|
| EP | 3408832 A1 * | 12/2018 | ............. A61B 34/10 |

OTHER PUBLICATIONS

A Review of Ultrasound and Computed Tomography Registration Approaches—2014 (Year: 2014).*

(Continued)

*Primary Examiner* — Nizar N Sivji
(74) *Attorney, Agent, or Firm* — Harness, Dickey & Pierce, P.L.C.

(57) ABSTRACT

Devices, systems, and methods used to register medical image data with anatomical positions are disclosed. The image data is captured by an imaging system over a period of time. The positions are determined by a tracking system over the period of time. The positions are averaged to determine an average position of the anatomy, which is then used for registration of the image data with the anatomy. Registration based on the average position can then be used to enhance the quality of 3D images of the anatomy, as well as to improve navigation for a surgical procedure.

14 Claims, 5 Drawing Sheets

(56) References Cited

U.S. PATENT DOCUMENTS

| | | |
|---|---|---|
| 2014/0094694 A1* | 4/2014 | Moctezuma de la Barrera .......... A61B 8/4254 600/407 |
| 2018/0046875 A1* | 2/2018 | Caluser .................. A61B 6/584 |
| 2019/0209046 A1 | 7/2019 | Addison et al. |
| 2019/0246954 A1* | 8/2019 | Adler, Jr. ............... G16H 50/50 |
| 2019/0366124 A1* | 12/2019 | Berlinger .................. G06T 7/74 |
| 2020/0046302 A1 | 2/2020 | Jacquel et al. |
| 2020/0187827 A1 | 6/2020 | Addison et al. |
| 2022/0284602 A1 | 9/2022 | Helm et al. |
| 2023/0008051 A1* | 1/2023 | Vilsmeier ............ A61N 5/1049 |

OTHER PUBLICATIONS

Reduction of motion artefacts in on-board cone beam CT by warping of projection images—2011 (Year: 2011).*

Orientation and Interpretation of CT Images—1983 (Year: 1983).*

T E Marchant et al, "Reduction of motion artefacts in on-board cone beam CT by warping of projection images", British Journal of Radiology, vol. 84, No. 999, Mar. 1, 2011, pp. 251-274.

International Search Report and Written Opinion corresponding to PCT/US2022/070888, Dated Jun. 7, 2022.

International Preliminary Report on Patentability with Written Opinion of the International Searching Authority (EPO), corresponding to PCT/US2022/070888, Date of Mailing Sep. 21, 2023 (9 pages).

* cited by examiner

SYSTEMS AND METHODS FOR MEDICAL IMAGERY ENHANCEMENT BY USE OF IMAGE GUIDANCE SYSTEM

RELATED APPLICATIONS

The present application claims priority to U.S. Provisional Application No. 63/149,739, filed on Feb. 16, 2021, and titled, "SYSTEMS AND METHODS FOR MEDICAL IMAGERY ENHANCEMENT BY USE OF IMAGE GUIDANCE SYSTEM," which is hereby incorporated by reference in its entirety.

TECHNICAL FIELD

The present disclosure relates generally to devices, systems, and methods used in the field of medical imagery. More specifically, the present disclosure relates to devices, systems, and methods used to register medical image data.

BRIEF DESCRIPTION OF THE DRAWINGS

The embodiments disclosed herein will become more fully apparent from the following description and appended claims, taken in conjunction with the accompanying drawings. These drawings depict only typical embodiments, which will be described with additional specificity and detail through use of the accompanying drawings in which:

DETAILED DESCRIPTION

Medical imagery of the anatomy of a patient can assist surgeons while operating on the patient during a surgical procedure. The imagery can help a surgeon visualize pertinent anatomical structures and accurately place surgical instruments during the procedure. An imaging system captures images of the patient's internal anatomy, such as cross-sectional views of the patient's organs.

Before a surgical procedure begins, the surgical team might capture a pre-operative imaging scan of the patient's anatomy using an imaging system. The imaging system can be a tomographic system, such as a magnetic resonance imaging (MRI) system or a computed tomography (CT) system. Often, the scan is taken while the patient lies on an operating table. In some embodiments, the imaging system encircles the patient about an axis and collects scanned image data from different angles around the patient. This image data is constructed into images, such as cross-sectional images of the patient's anatomy.

A medical imagery scan can be performed over a period of time. In some embodiments, the period of time that a scan lasts is approximately 18 seconds. In some embodiments, the period of time is approximately 28 seconds. During the period of time of the scan, an array of image data is collected from multiple viewpoints corresponding to various points in time throughout the period of time of the scan.

After the scan is complete, the image data may be registered with the patient anatomy based on a position or positions of the anatomy during the period of time of the scan. Registration involves determining a coordinate transform that maps the image data into an appropriate coordinate system to overlay the image data over a current image of the patient for navigation by the surgeon. Navigation includes the process of identifying a pose (e.g., location and orientation) of a particular anatomical structure and/or of a surgical instrument.

During registration of image data with patient anatomy, the pose of the anatomy is used to determine the coordinate transform. Ordinarily, the pose selected for registration is the initial pose of the patient anatomy at the outset of the scan. During the scan, however, the pose of the patient anatomy relative to the imaging system can change. Causes of such change include vibration of the imaging system and movement of the patient. Changes in pose may cause errors in the registration process that can be deleterious for navigation and ultimately for the surgical procedure.

Embodiments herein may improve the registration process by collecting position data during the scan and using the position data to determine a more accurate pose of the patient anatomy in the pre-operative scan on which to base the registration. Position data comprises a distance between the patient anatomy and the imaging system. Rather than base the registration on a pose determined before or at the beginning of the scan, the registration can be accomplished based on a pose or poses that is or are determined during the scan. For example, an average position of the patient anatomy can be calculated from the position data collected during the scan. Using that average position for the pose inputted into the registration process may improve the results of the registration by reducing a maximum displacement. Consequently, navigation can be improved.

Embodiments may be understood by reference to the drawings, wherein like parts are designated by like numerals throughout. It will be readily understood by one of ordinary skill in the art having the benefit of this disclosure that the components of the embodiments, as generally described and illustrated in the figures herein, could be arranged and designed in a wide variety of different configurations. Thus, the following more detailed description of various embodiments, as represented in the figures, is not intended to limit the scope of the disclosure, but is merely representative of various embodiments. While the various aspects of the embodiments are presented in drawings, the drawings are not necessarily drawn to scale unless specifically indicated.

Figure 1:
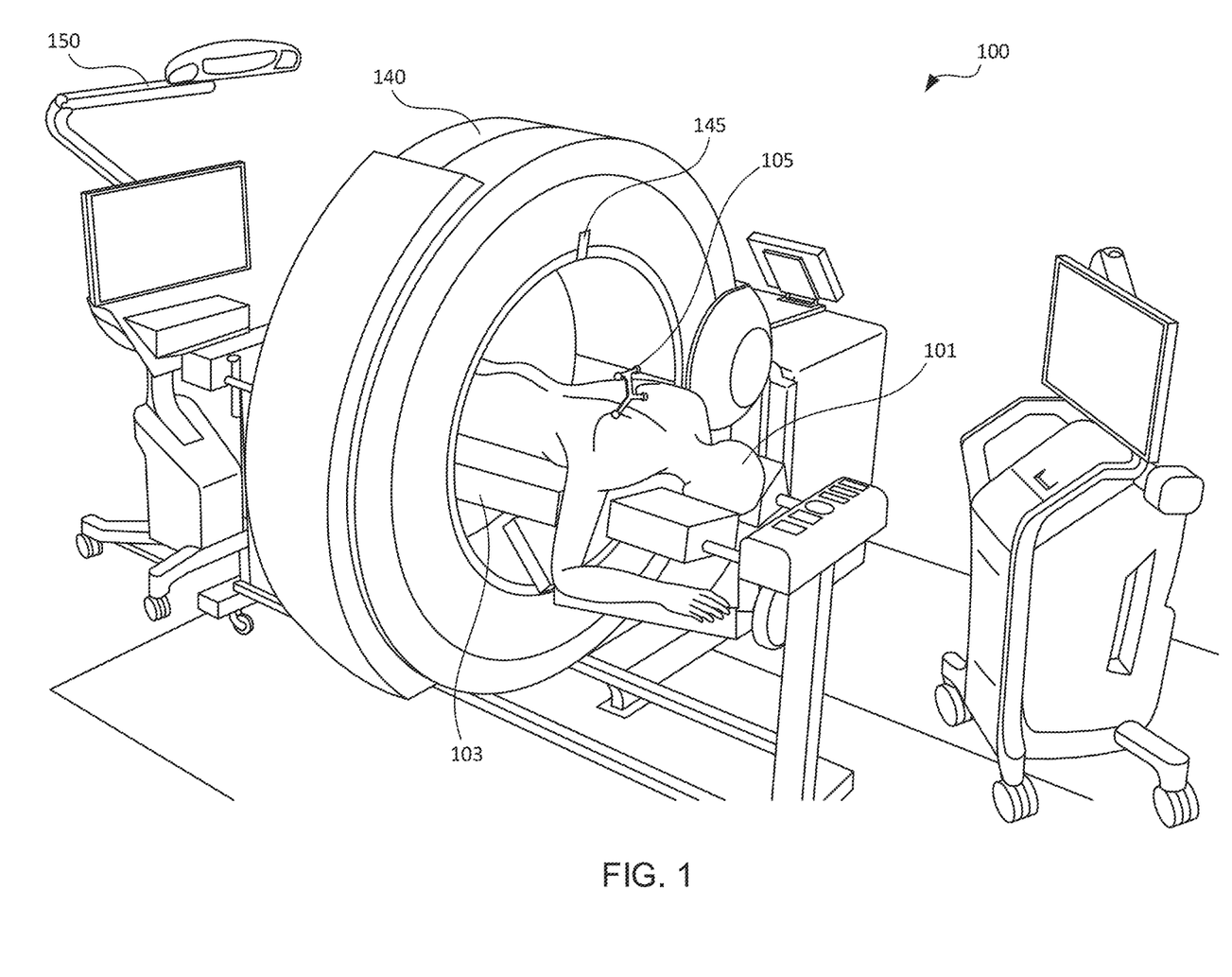
FIG. 1 is a perspective view of an operating room with an imaging system collecting image data of patient anatomy and a tracking system determining position data of the patient anatomy in accordance with one embodiment.

FIG. 1 depicts a perspective view of an imaging and position tracking system 100. Within an operating room is an operating table 103, on which a patient 101 lies. Before a surgical procedure begins, an imaging system 140 is positioned around the patient 101 to run a scan and collect imagery (e.g., a pre-operative scan) of the patient's anatomy. A tracking system 150 may be used to monitor the scene and observe the movements of a patient tracker 105 and of an imaging system tracker 145. The tracking system 150 may determine relative positions throughout the scan between the patient tracker 105 and the imaging system tracker 145. The relative positions between the patient tracker 105 and the imaging system tracker 145 can be converted into relative positions between the patient anatomy and the imaging system 140. Such conversion may be based on known positional relationships between the imaging system 140 and the imaging system tracker 145, and between the patient anatomy and the patient tracker 105.

The tracking system 150 can be an image guidance system. An image guidance system uses optical technology to detect and monitor the poses of various trackers. In particular, the image guidance system can detect a patient tracker 105, an instrument tracker, and an imaging system tracker 145.

A patient tracker 105 is a device that the surgeon couples to the patient 101. The patient tracker 105 can be a reference frame. A reference frame can be a rigid object with distinct surfaces on it that can be detected by the tracking system 150. The reference frame can rest on the body of the patient 101, be coupled to a clamp used by the surgeon to restrain the patient 101 during the procedure, or be coupled to the patient 101 in some other way. The tracking system 150 determines poses of the reference frame in three-dimensional space. Determination of poses of the reference frame can happen throughout the period of time of the scan, as well as after the scan during the surgical procedure. These poses may be included in an array of position data collected and stored by the tracking system 150.

An instrument tracker is a device coupled to or part of a surgical instrument. It can be a rigid object with distinct surfaces for detection by the tracking system 150, similar to the patient tracker 105. The tracking system 150 determines poses of the instrument tracker in three-dimensional space during the surgical procedure.

In addition to detecting a patient tracker 105 coupled to the patient 101 and an instrument tracker coupled to a surgical instrument, the tracking system 150 can detect an imaging system tracker 145 embedded within or coupled to the imaging system 140. The tracking system 150 can determine poses of the imaging system tracker 145 in three-dimensional space throughout the period of time of a preoperative scan. To do this, the tracking system 150 can employ a similar method to that used to detect and track the patient tracker 105.

The tracking system 150 can detect and track the poses of the patient tracker 105 and the imaging system tracker 145 throughout the duration of the scan. The poses of these trackers can be compared with each other to determine relative positions of the patient tracker 105 to the imaging system tracker 145.

The relative positions of the patient tracker 105 and the imaging system tracker 145 may be recorded. An array of these positions of the patient tracker 105 relative to the imaging system 140 can be determined throughout the duration of the scan. Such an array of relative positions may be part of the position data determined by the tracking system 150.

The position data comprises a distance between the patient anatomy and the imaging system. The position data can include both rectangular and rotational positions. It can include other states such as velocities. It can be represented in any of various coordinate systems. For example, the position data can include data in Cartesian coordinate form, spherical coordinate form, Euler angle form, direction cosine form, quaternion form, and/or other forms.

The position data can be used to transform the image data into a coordinate system that corresponds with the live imagery of a patient that the surgeon sees on a display device during the surgical procedure. This process is known as registration. Registration is the determination of a mapping between the coordinates in one space and those in another (e.g., a pre-operative scan and live imagery of a patient during an operation), such that points in the two spaces that correspond to the same anatomical point are mapped to each other. For example, the imaging system may map a pre-operative scan and live imagery of a patient during an operation to overlay the pre-operative scan on a graphical user interface. The registration process may include determining a coordinate transform that maps the image data and the position data into a uniform coordinate system in order to properly reconstruct the imagery and provide navigational information to the surgeon.

Navigation may include the method used by the surgeon to track the poses of the patient anatomy and the surgical instruments. During a surgical procedure, an instrument can be tracked in an object or subject space. In various embodiments the subject space can be a patient space defined by a patient 101. The location of the instrument that is tracked can be displayed on the display device relative to an image of the patient 101. The surgeon can track an instrument relative to the patient 101 based upon the registered image data, where the tracking system 150 tracks the instrument and an icon representing the instrument is super-imposed on the image seen by the surgeon.

A problem that surgeons encounter while registering image data with patient anatomy is noise in the image data. A common source of noise is movement within the operating room that negatively affects the image data during a scan. For example, the imaging system 140 can vibrate, which causes the equipment in the imaging system 140, such as transceivers or detectors, to vibrate and blur the data collected. As another example of a source of noise in the image data, the patient can move during a scan. One type of patient motion is from breathing. With air entering and exiting the patient's lungs, the patient's chest or back will move up and down. This can be particularly problematic during a scan of the patient's spine, for example, because even millimeter movements of the spine can lead to incorrect navigational information based on the image data. Another type of motion of the patient can be from voluntary or involuntary movement of a part of the body during the scan. For example, in a procedure in which the patient is awake, the patient's head may move from side to side by several millimeters. These kinds of motions add noise to the image data and can have significant adverse consequences on registration, navigation, and 3D image reconstruction. When the image data collected by the imaging system is noisy, the navigational information to the surgeon can contain undesirable errors. For example, if the position of the patient during a pre-operative scan is not what is expected, the registration process may cause the overlay of the pre-operative scan during surgery to be off which may provide the surgeon with incorrect navigation data. Additionally, the reconstructed 3D images can be blurry.

Figure 2:
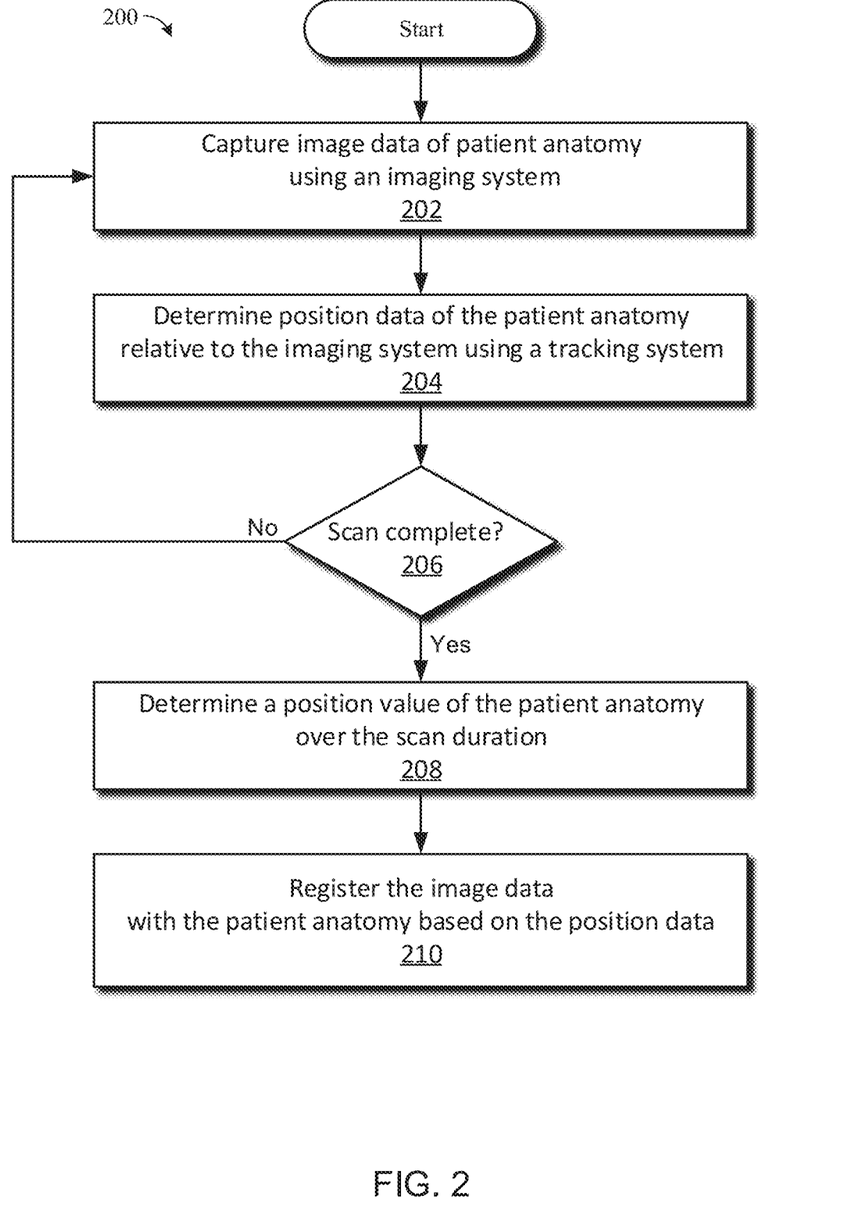
FIG. 2 is a flow chart of a method for registering image data with patient anatomy in accordance with one embodiment.

FIG. 2 is a flow chart of a method 200 for registering image data with patient anatomy based on position data. The method 200 may be used by an imaging and position tracking system such as shown in FIG. 1. The method 200 may begin with a scan carried out by an imaging system. During the scan, an imaging system may capture 202 image data of patient anatomy.

Concurrently with the imagery capture, a tracking system may determine 204 position data. The position data may include the pose of the patient anatomy relative to the imaging system. In some embodiments, a tracking system may comprise an image guidance system that optically tracks a pose of a patient tracker relative to a position of the imaging system. For example, a tracking system may identify and track an imaging system tracker coupled to the imaging system and a patient tracker coupled to the patient. The tracking system may determine the position data based on locations of the imaging system tracker and locations of the patient tracker during the period of time. The image data and position data may be repeatedly captured until the scan is completed 206.

After completion of the scan, a position value of the patient anatomy over the scan duration may be determined 208 by the imaging and position tracking system. The position value of the patient anatomy may be incorporated into the position data. The imaging and position tracking system may use the position data as part of a registration procedure. For example, the imaging and position tracking system may determine an average position of the patient anatomy over the scan duration. In some embodiments, averaging the position data may be carried out by taking the average value of an array of poses of the patient anatomy relative to the imaging system that correspond with an array of time data associated with the period of time of the scan. In some embodiments, the averaging can be done with respect to each component of pose (including each component of, for example, location and orientation) in the coordinate frame by which the position data is stored. In some embodiments, the averaging may be done with respect to only certain of the components of pose in the coordinate frame by which the position data is stored. In some embodiments, the averaging may be done in a different coordinate system than the one by which the position data is stored. In some embodiments, the averaging can comprise using an arithmetic mean. In some embodiments, the averaging can comprise using a geometric mean.

In some embodiments, the averaging can be carried out by integrating the position data over the period of time of the scan, and dividing the integral by the total time of the period of time of the scan. For example, the plot of FIG. 5 could be integrated to calculate an area with a distance-time unit, and then that area could be divided by the duration of the scan. The resulting average displacement will have a value greater than zero, but less than the maximum displacement point during the scan. This average displacement can be incorporated with the position data to determine an average position.

In some embodiments, the averaging may be done with respect to a magnitude or other norm of the position data. In some embodiments, the averaging may comprise an unconventional averaging process. In some embodiments, the averaging may comprise a weighting method. A weighting method may include a time-weighted or a position-weighted calculation. For example, the averaging process may give special weight to position data collected near the beginning time and the end time of the pre-operative scan, and may give less weight to position data collected near the middle of the scan's duration. As another example, the averaging process may give special weight to location values corresponding with less erratic orientation values, and may deemphasize location values corresponding with orientation values deviating greatly from an expected or calculated orientation of anatomy. The averaging process may comprise an iterative calculation process that successively updates the weights of the weighting method and refines the position data.

Based on the position data, the image data may be registered 210 with the patient anatomy. More specifically, the registration 210 can be based on an average position of the patient anatomy. After the array of poses of patient anatomy is averaged to determine an average position, the average position can be used to register 210 the image data with the patient anatomy. This is in contrast with using a predetermined pose that the tracking system determines before the scan is run. The predetermined pose would ordinarily be detected at the outset of the scan, but it might be an outlier among the various actual poses throughout the scan. The average position can better represent the actual poses of the patient anatomy for purposes of registration and image reconstruction.

Figure 3:
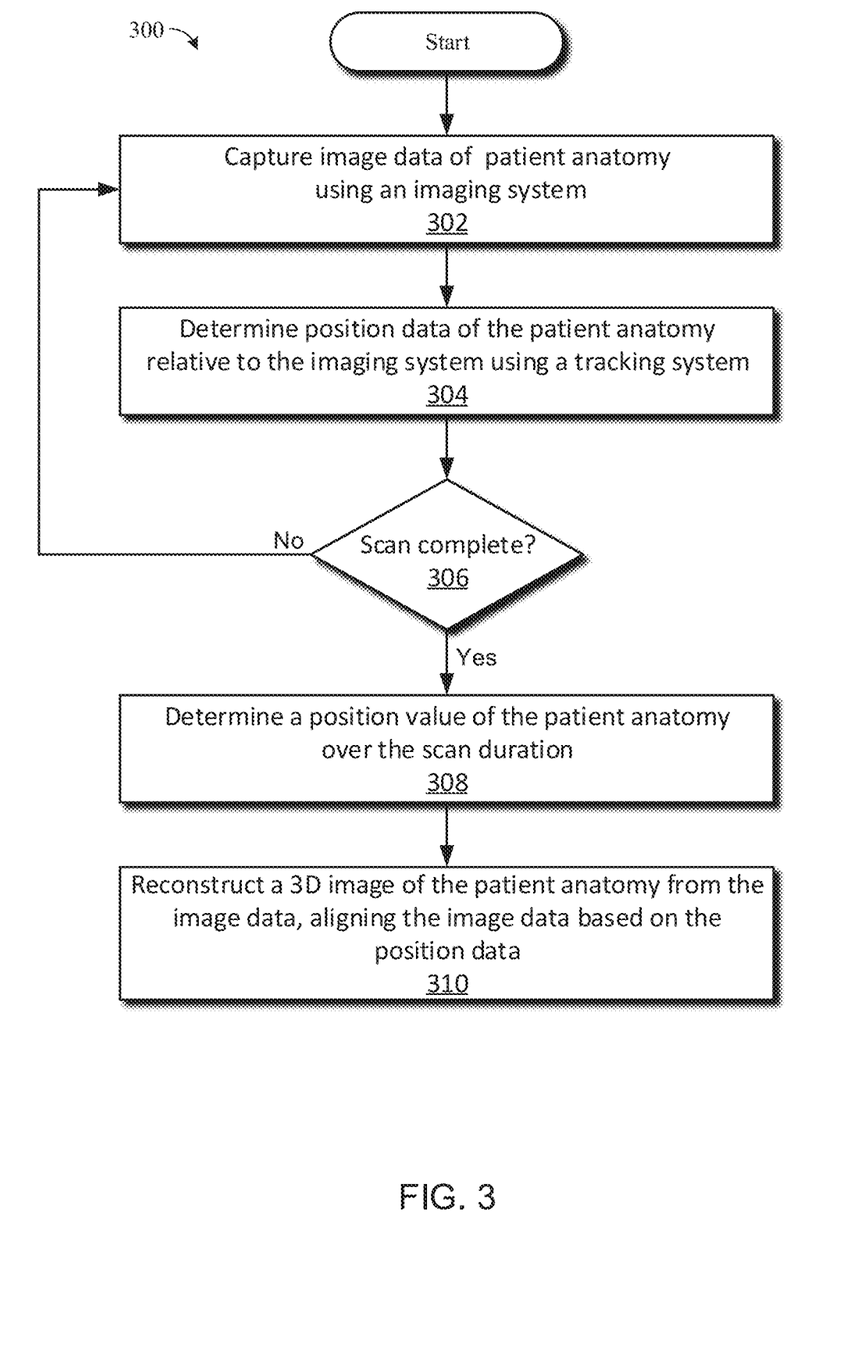
FIG. 3 is a flow chart of a method for reconstructing a three-dimensional (3D) image of patient anatomy in accordance with one embodiment.

FIG. 3 is a flow chart of a method 300 for reconstructing a 3D image of patient anatomy. The method 300 may be used by an imaging and position tracking system such as shown in FIG. 1. The method 300 begins with a scan carried out by an imaging system. During the scan, the imaging system may capture 302 image data of patient anatomy.

Concurrently with the imagery capture, a tracking system may determine 304 position data of the patient anatomy relative to the imaging system. The position data may include the pose of the patient anatomy relative to the imaging system. In some embodiments, a tracking system may comprise an image guidance system that optically tracks a pose of a patient tracker relative to a position of the imaging system. For example, a tracking system may identify and track an imaging system tracker coupled to the imaging system and a patient tracker coupled to the patient. The tracking system may determine the position data based on locations of the imaging system tracker and locations of the patient tracker during the period of time. The image data and position data may be repeatedly captured until the scan is completed 306.

After completion of the scan, a position value of the patient anatomy over the scan duration may be determined 308 by the imaging and position tracking system. The position value of the patient anatomy may be incorporated into the position data. Finally, a 3D image of the patient anatomy may be reconstructed 310 by the imaging and position tracking system from the image data based on the position data. For example, the imaging and position tracking system may align the image data based on the position data. In some embodiments, the alignment may be based on the position value. In some embodiments, the alignment may be based on an average position.

In some embodiments, averaging the position data may be carried out by taking the average value of an array of poses of the patient anatomy relative to the imaging system that correspond with an array of time data associated with the period of time of the scan. In some embodiments, the averaging can be done with respect to each component of pose (including each component of, for example, location and orientation) in the coordinate frame by which the position data is stored. In some embodiments, the averaging may be done with respect to only certain of the components of pose in the coordinate frame by which the position data is stored. In some embodiments, the averaging may be done in a different coordinate system than the one by which the position data is stored. In some embodiments, the averaging can comprise using an arithmetic mean. In some embodiments, the averaging can comprise using a geometric mean.

In some embodiments, the averaging can be carried out by integrating the position data over the period of time of the scan, and dividing the integral by the total time of the period of time of the scan. For example, the plot of FIG. 5 could be integrated to calculate an area with a distance-time unit, and then that area could be divided by the duration of the scan. The resulting average displacement will have a value greater than zero, but less than the maximum displacement point during the scan. This average displacement can be incorporated with the position data to determine an average position.

In some embodiments, the averaging may be done with respect to a magnitude or other norm of the position data. In some embodiments, the averaging may comprise an unconventional averaging process. In some embodiments, the averaging may comprise a weighting method. A weighting method may include a time-weighted or a position-weighted calculation. For example, the averaging process may give special weight to position data collected near the beginning time and the end time of the pre-operative scan, and may give less weight to position data collected near the middle of the scan's duration. As another example, the averaging process may give special weight to location values corresponding with less erratic orientation values, and may deemphasize location values corresponding with orientation values deviating greatly from an expected or calculated orientation of anatomy. The averaging process may comprise an iterative calculation process that successively updates the weights of the weighting method and refines the position data.

Using the average position of patient anatomy determined after the scan can reduce blurriness of the 3D images that are reconstructed 310 from the image data. It can also increase the accuracy of navigation during the surgical procedure. While at some increments of time during the scan, the average position may be farther from some of the actual poses than a predetermined pose would be, other actual poses during the scan may be better represented by the average position, and on the whole, the average position may be better suited for registration than the predetermined pose. The average position may reduce the magnitude of the error caused by movement of the patient or imaging system.

Figure 4:
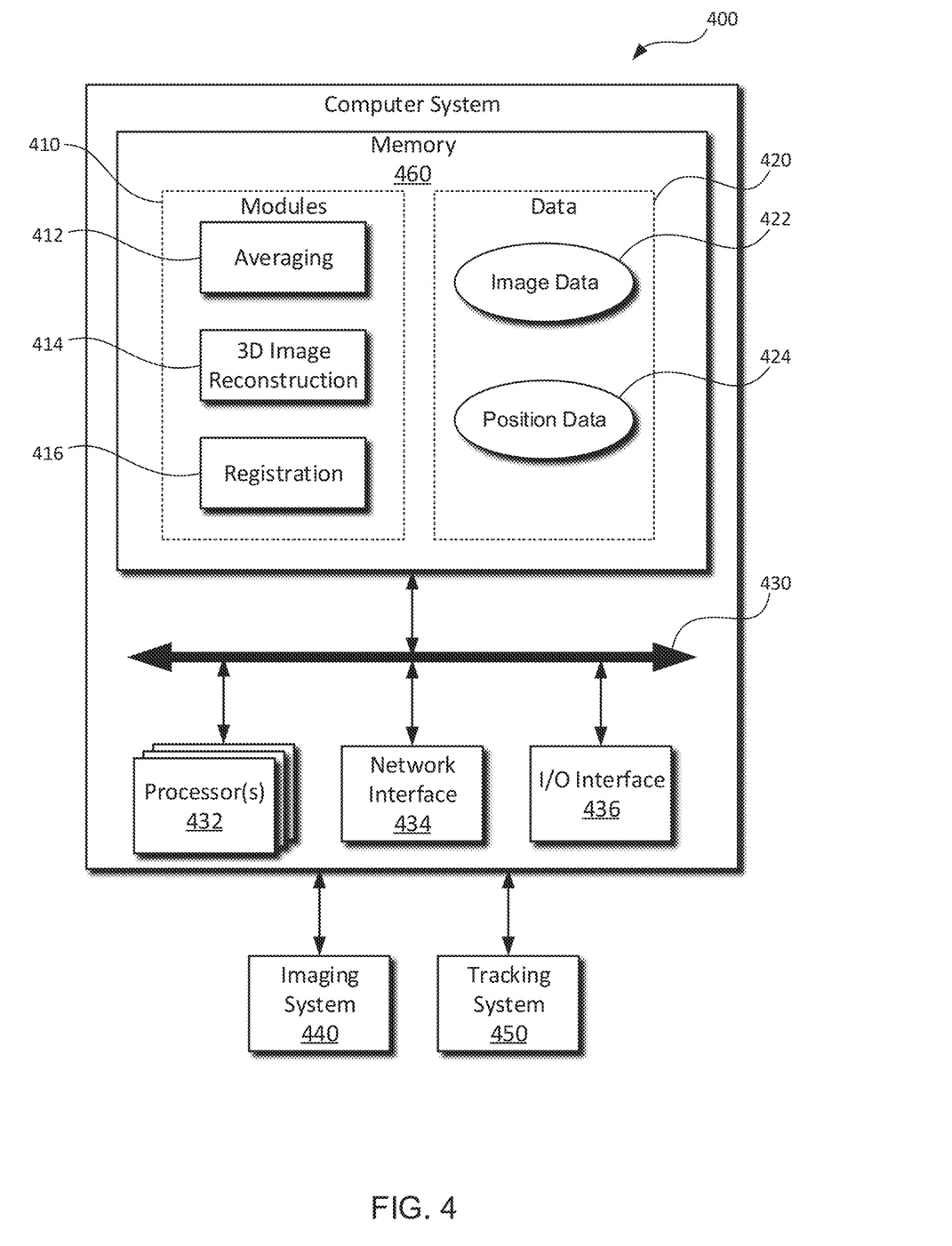
FIG. 4 is a block diagram of a computing system configured for registration and 3D image reconstruction in accordance with one embodiment.

FIG. 4 is a block diagram of a computing system 400 configured for registration and 3D image reconstruction. The computing system 400 can comprise a computing apparatus that includes memory 460, one or more processors 432, a network interface 434, an input/output interface 436, and a system bus 430.

The one or more processors 432 may include one or more general purpose devices, such as a standard microprocessor. The one or more processors 432 may include a special purpose processing device, such as ASIC, SoC, SiP, FPGA, PAL, PLA, FPLA, PLD, or other customized or programmable device. The one or more processors 432 can perform distributed (e.g., parallel) processing to execute or otherwise implement functionalities of the presently disclosed embodiments. The one or more processors 432 may run a standard operating system and perform standard operating system functions. It is recognized that any standard operating system may be used.

The memory 460 may include static RAM, dynamic RAM, flash memory, one or more flip-flops, ROM, CD-ROM, DVD, disk, tape, or magnetic, optical, or other computer storage mediums. The memory 460 may include a plurality of program modules 410 and program data 420. The memory 460 may be local to the computing system 400, as shown, or may be distributed and/or remote relative to the computing system 400.

The memory 460 may include the program data 420. Data generated or used by the computing system 400, such as by the program modules 410 or other modules, may be stored on the memory 460, for example, as stored program data 420. The program data 420 may be organized as one or more databases. The program data 420 may include image data 422 collected by an imaging system 440 and position data 424 collected by a tracking system 450. The position data 424 may comprise the distance between a tracker on a patient and a tracker on the imaging system over a duration of a scan.

The program modules 410 may include all or portions of other elements of the computing system 400. The program modules 410 may run multiple operations concurrently or in parallel by or on the one or more processors 432. In some embodiments, portions of the disclosed modules, components, and/or facilities are embodied as executable instructions embodied in hardware or firmware, or stored on a non-transitory, machine-readable storage medium. The executable instructions may comprise computer program code that, when executed by a processor and/or computing device, cause a computing system to implement certain processing steps, procedures, and/or operations, as disclosed herein. The modules, components, and/or facilities disclosed herein may be implemented and/or embodied as a driver, a library, an interface, an API, FPGA configuration data, firmware (e.g., stored on an EEPROM), and/or the like. In some embodiments, portions of the modules, components, and/or facilities disclosed herein are embodied as machine components, such as general and/or application-specific devices, including, but not limited to: circuits, integrated circuits, processing components, interface components, hardware controller(s), storage controller(s), programmable hardware, FPGAs, ASICs, and/or the like. Accordingly, the modules disclosed herein may be referred to as controllers, layers, services, engines, facilities, drivers, circuits, subsystems, and/or the like. The program modules 410 may comprise an averaging module 412, a 3D image reconstruction module 414, and a registration module 416. The averaging module 412 may average the position data 424. The 3D image reconstruction module 414 may use the position data 424 to compile the image data 422 into a 3D image. For example, the position data 424 may be used to align the image data 422. The registration module 416 may use the position data 424 to register the image data 422.

The input/output interface 436 may facilitate user interaction with one or more input devices and/or one or more output devices. The input device(s) may include a keyboard, mouse, touchscreen, light pen, tablet, microphone, sensor, or other hardware with accompanying firmware and/or software. The output device(s) may include a monitor or other display, printer, speech or text synthesizer, switch, signal line, speaker, or other hardware with accompanying firmware and/or software. In some embodiments, the input/output interface 436 is a touchscreen.

The network interface 434 may facilitate communication with other computing devices and/or networks and/or other computing and/or communications networks. The network interface 434 may be equipped with conventional network connectivity, such as, for example, Ethernet (IEEE 1102.3), Token Ring (IEEE 1102.5), Fiber Distributed Datalink Interface (FDDI), or Asynchronous Transfer Mode (ATM). Further, the network interface 434 may be configured to support a variety of network protocols such as, for example, Internet Protocol (IP), Transfer Control Protocol (TCP), Network File System over UDP/TCP, Server Message Block (SMB), Common Internet File System (CIFS), Hypertext Transfer Protocols (HTTP), Direct Access File System (DAFS), File Transfer Protocol (FTP), Real-Time Publish Subscribe (RTPS), Open Systems Interconnection (OSI) protocols, Simple Mail Transfer Protocol (SMTP), Secure Shell (SSH), Secure Socket Layer (SSL), and so forth.

The system bus 430 may facilitate communication and/or interaction between the other components of the computing system 400, including the one or more processors 432, the memory 460, the input/output interface 436, and the network interface 434.

Figure 5:
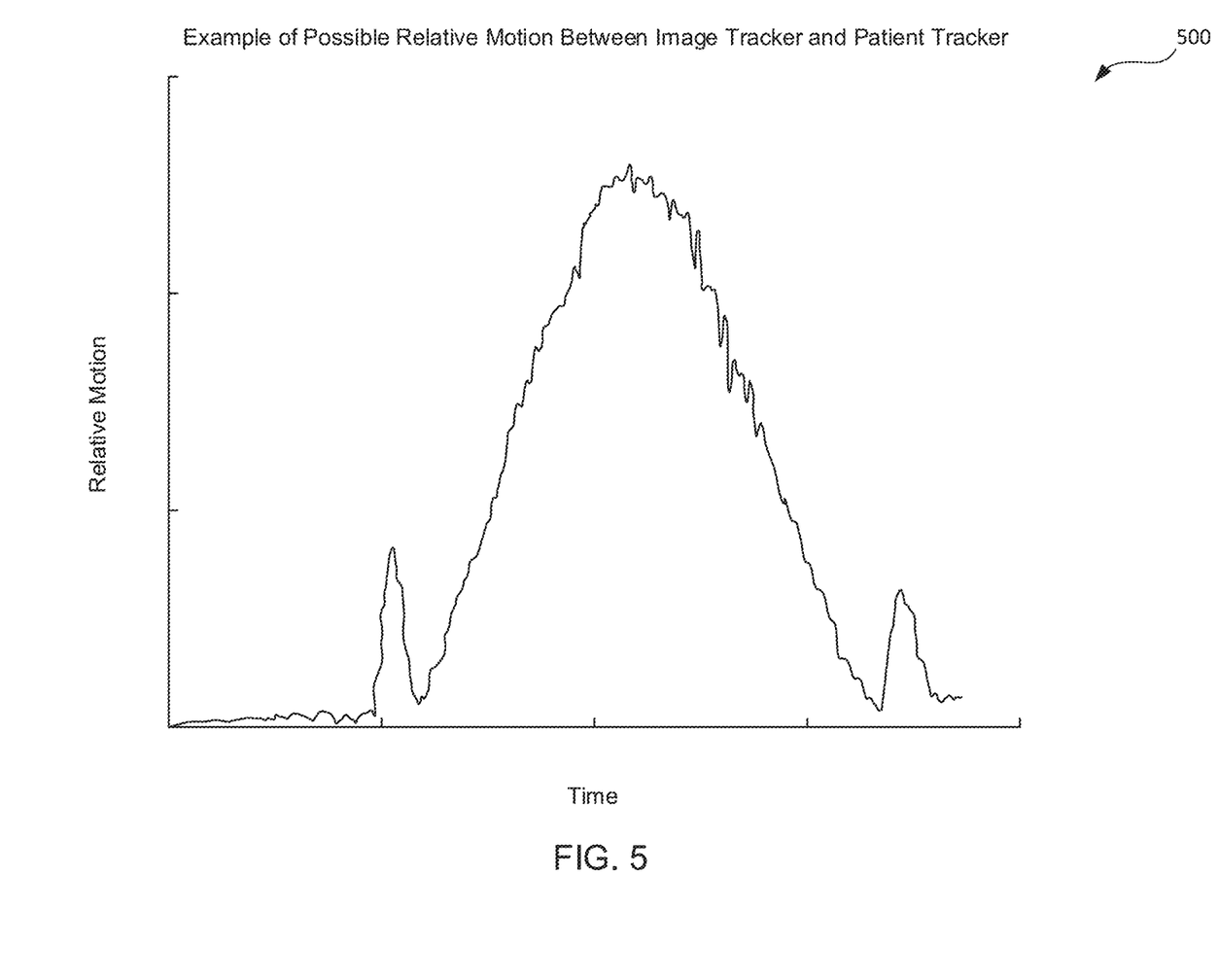
FIG. 5 is a graph of relative motion of patient anatomy during an imagery scan of the patient anatomy in accordance with one embodiment.

FIG. 5 shows an example plot 500 of position data from a scan in which a relative distance between a patient and an imaging system changed throughout the duration of the scan. Movements such as those represented in FIG. 5 add to the registration error and cause problems for navigation and image reconstruction.

Errors in registration are problematic because they cause the navigational and imagery information to be misaligned with the actual anatomy of the patient. For example, the surgeon might place an instrument in a particular location based on what the surgeon sees displayed on the display device. But the perceived pose of the patient anatomy may be different from the actual pose of the patient anatomy, leading to misplacement of the surgical instrument. Misplacement of instruments can cause serious injuries in surgery, even if the registration errors are small. Thus, it is desirable to enhance registration by using a registration position that decreases these errors.

Any methods disclosed herein comprise one or more steps or actions for performing the described method. The method steps and/or actions may be interchanged with one another. In other words, unless a specific order of steps or actions is required for proper operation of the embodiment, the order and/or use of specific steps and/or actions may be modified.

It will be appreciated that various features are sometimes grouped together in a single embodiment, figure, or description thereof for the purpose of streamlining the disclosure. Many of these features may be used alone and/or in combination with one another.

The phrases "coupled to" and "in communication with" refer to any form of interaction between two or more entities, including mechanical, electrical, magnetic, electromagnetic, fluid, and thermal interaction. Two components may be coupled to or in communication with each other even though they are not in direct contact with each other. For example, two components may be coupled to or in communication with each other through an intermediate component.

References to approximations are made throughout this specification, such as by use of the term "substantially." For each such reference, it is to be understood that, in some embodiments, the value, feature, or characteristic may be specified without approximation. For example, where qualifiers such as "about" and "substantially" are used, these terms include within their scope the qualified words in the absence of their qualifiers. For example, where the term "substantially perpendicular" is recited with respect to a feature, it is understood that in further embodiments the feature can have a precisely perpendicular configuration.

Similarly, in the above description of embodiments, various features are sometimes grouped together in a single embodiment, figure, or description thereof for the purpose of streamlining the disclosure. This method of disclosure, however, is not to be interpreted as reflecting an intention that any claim require more features than those expressly recited in that claim. Rather, as the following claims reflect, inventive aspects lie in a combination of fewer than all features of any single foregoing disclosed embodiment.

The claims following this written disclosure are hereby expressly incorporated into the present written disclosure, with each claim standing on its own as a separate embodiment. This disclosure includes all permutations of the independent claims with their dependent claims. Moreover, additional embodiments capable of derivation from the independent and dependent claims that follow are also expressly incorporated into the present written description.

Without further elaboration, it is believed that one skilled in the art can use the preceding description to utilize the invention to its fullest extent. The claims and embodiments disclosed herein are to be construed as merely illustrative and exemplary, and not a limitation of the scope of the present disclosure in any way. It will be apparent to those having ordinary skill in the art, with the aid of the present disclosure, that changes may be made to the details of the above-described embodiments without departing from the underlying principles of the disclosure herein. In other words, various modifications and improvements of the embodiments specifically disclosed in the description above are within the scope of the appended claims. Moreover, the order of the steps or actions of the methods disclosed herein may be changed by those skilled in the art without departing from the scope of the present disclosure. In other words, unless a specific order of steps or actions is required for proper operation of the embodiment, the order or use of specific steps or actions may be modified. The scope of the invention is therefore defined by the following claims and their equivalents.

The invention claimed is:

1. A method for registering image data with anatomy of a patient, the method comprising:
    capturing, via an imaging system, image data of patient anatomy for a period of time;
    determining, via a tracking system, position data of the patient anatomy relative to the imaging system by tracking the position of the patient anatomy and imaging system during the period of time that the image data is being captured;
    tracking, via the tracking system, an imaging system tracker coupled to the imaging system and a patient tracker coupled to the patient, wherein the position data is based on locations of the imaging system tracker and locations of the patient tracker during the period of time;
    averaging the position data over the period of time to determine an average position of the patient anatomy relative to the imaging system; and
    registering the image data with the patient anatomy based on the position data;
    wherein the position data used to register the image data with the patient anatomy is the average position of the patient anatomy.

2. The method according to claim 1, wherein the patient tracker is a reference frame used for navigation.

3. The method according to claim 1, wherein the tracking system is an image guidance system.

4. The method according to claim 1, further comprising reconstructing a 3D image of the patient anatomy from the image data and the position data.

5. The method according to claim 4, wherein the position data is used to align the image data.

6. The method according to claim 1, wherein the average position is calculated with each component of pose including location and orientation.

7. The method according to claim 1, wherein the average position is calculated by integrating the position data over the period of time that the image data is being captured and dividing by the total time period of the scan.

8. The method according to claim 1, wherein the average position is determined by a time-weighted or a position-weighted calculation.

9. A method for registering image data with anatomy of a patient, the method comprising:
- capturing, via an imaging system, image data of patient anatomy for a period of time;
- determining, via a tracking system, position data of the patient anatomy relative to the imaging system by tracking the position of the patient anatomy and the imaging system during the period of time that the image data is being captured;
- tracking, via the tracking system, an imaging system tracker coupled to the imaging system and a patient tracker coupled to the patient wherein the position data is based on locations of the imaging system tracker and locations of the patient tracker during the period of time:
- averaging the position data over the period of time to determine an average position of the patient anatomy relative to the imaging system; and
- reconstructing a 3D image of the patient anatomy from the image data and the position data;
- wherein the position data used to reconstruct the 3D image of the patient anatomy is the average position of the patient anatomy.

10. The method according to claim 9, wherein the patient tracker is a reference frame used for navigation.

11. The method according to claim 9, wherein the tracking system is an image guidance system.

12. The method according to claim 9, wherein the position data is used to align the image data.

13. A computing apparatus comprising:
- a processor; and
- memory storing instructions that, when executed by the processor, configure the apparatus to:
- capture, via an imaging system, image data of patient anatomy for a period of time;
- determine, via a tracking system, position data of the patient anatomy
- relative to the imaging system by tracking the position of the patient anatomy and the imaging system during the period of time that the image data is being captured;
- average the position data over the period of time to determine an average position of the patient anatomy relative to the imaging system; and
- register the image data with the patient anatomy based on the position data;
- wherein the position data used to register the image data with the patient anatomy is the average position of the patient anatomy;
- wherein the memory storing instructions further configure the pparatus to track, via the tracking system, an imaging system tracker coupled to the imaging system and a patient tracker coupled to the patient, and whereir the position data is based on locations of the imaging system tracker and locations of the patient tracker during the period of time.

14. The computing apparatus according to claim 13, wherein the patient tracker is a reference frame used for navigation.

* * * * *